US009683921B2

(12) United States Patent
Halden et al.

(10) Patent No.: US 9,683,921 B2
(45) Date of Patent: Jun. 20, 2017

(54) DEVICES AND METHODS FOR DETERMINATION OF BIOAVAILABILITY OF POLLUTANTS

(75) Inventors: Rolf U. Halden, Phoenix, AZ (US); Isaac B. Roll, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 757 days.

(21) Appl. No.: 14/112,711

(22) PCT Filed: Apr. 17, 2012

(86) PCT No.: PCT/US2012/033912
§ 371 (c)(1),
(2), (4) Date: Dec. 12, 2013

(87) PCT Pub. No.: WO2012/145299
PCT Pub. Date: Oct. 26, 2012

(65) Prior Publication Data
US 2014/0102182 A1 Apr. 17, 2014

Related U.S. Application Data

(60) Provisional application No. 61/476,865, filed on Apr. 19, 2011, provisional application No. 61/481,424, filed on May 2, 2011.

(51) Int. Cl.
*B01D 15/14* (2006.01)
*B01D 24/40* (2006.01)
(Continued)

(52) U.S. Cl.
CPC ......... *G01N 15/0631* (2013.01); *B01D 15/08* (2013.01); *B01D 15/14* (2013.01);
(Continued)

(58) Field of Classification Search
CPC ........ B01D 15/08; B01D 15/10; B01D 15/14; B01D 24/00; B01D 24/007; B01D 24/16;
(Continued)

(56) References Cited

U.S. PATENT DOCUMENTS 4,628,748 A    12/1986   Jogan et al.
4,717,473 A *   1/1988   Burge ................... E21B 23/06
                                                                 166/147

(Continued)

OTHER PUBLICATIONS

PCT/US2012/033912, International Preliminary Report on Patentability, Oct. 22, 2013.
(Continued)

*Primary Examiner* — Joseph Drodge
(74) *Attorney, Agent, or Firm* — George A. Leone; Citadel Patent Law

(57) ABSTRACT

Contaminant mass collection in saturated sedimentary environments for bioavailability determination. A casing includes a screen between the environment that is subject to sampling, such as a saturated sediment and the device itself. The casing includes a water intake zone, a pump, and sorptive media. The water intake zone, the pump, the screen and the sorptive media, are all operably linked in sequence. The screened casing is secured to form an in situ device; the screen is in fluid communication with the water intake zone and excludes endemic sediments and aquatic life. The in situ device is deployed in the saturated sedimentary environment. The pump operates to concentrate analytes from the selected environment in the sorptive media, where the concentrated analytes include the analyte mass of time-weighted fluid samples.

19 Claims, 16 Drawing Sheets

(51) Int. Cl.
*B01D 35/26* (2006.01)
*B01D 36/02* (2006.01)
*B01D 61/58* (2006.01)
*C02F 9/00* (2006.01)
*C02F 1/44* (2006.01)
*G01N 1/14* (2006.01)
*G01N 1/16* (2006.01)
*G01N 1/18* (2006.01)
*G01N 1/40* (2006.01)
*E02D 1/06* (2006.01)
*G01N 15/06* (2006.01)
*G01N 5/02* (2006.01)
*B01D 15/08* (2006.01)

(52) U.S. Cl.
CPC ............ *B01D 24/40* (2013.01); *B01D 35/26* (2013.01); *B01D 36/02* (2013.01); *B01D 61/58* (2013.01); *C02F 1/444* (2013.01); *E02D 1/06* (2013.01); *G01N 1/14* (2013.01); *G01N 1/16* (2013.01); *G01N 1/18* (2013.01); *G01N 1/405* (2013.01); *G01N 5/02* (2013.01)

(58) Field of Classification Search
CPC ........ B01D 24/38; B01D 24/40; B01D 35/26; B01D 35/30; B01D 35/31; B01D 29/0029; B01D 29/0047; B01D 29/0052; B01D 29/005; B01D 35/02; B01D 36/00; B01D 36/02; B01D 37/00; B01D 61/14; B01D 61/142; B01D 61/145; B01D 61/147; B01D 61/18; B01D 61/20; B01D 61/58; B01D 2311/04; B01D 2311/26; B01D 2311/2627; B01D 2311/2626; B01D 2311/2649; B01D 2313/243; C02F 1/001; C02F 1/002; C02F 1/26; C02F 1/28; C02F 1/44; C02F 1/444; C02F 9/00; C02F 9/005; G01N 1/14; G01N 1/16; G01N 1/18; G01N 1/40; G01N 1/4055; G01N 1/405; G01N 1/4077; G01N 2001/1445; G01N 2001/1454; G01N 2001/1463; G01N 2001/4061; G01N 2001/4083; G01N 2001/4088; G01N 5/02; G01N 15/0618; G01N 15/0631; G01N 1/10; G01N 1/4005; G01N 1/4011; G01N 1/4016; E02D 1/04; E02D 1/06

USPC ....... 73/61.55, 61.71, 61.73, 863.21, 863.23, 73/863.71, 863.83, 864.34; 210/198.2, 210/263, 264, 266, 282, 638, 641, 650, 210/651, 660, 662, 663, 669, 690, 691; 422/527, 534, 535, 70; 436/174, 177, 436/178

See application file for complete search history.

(56) References Cited

U.S. PATENT DOCUMENTS

| | | | |
|---|---|---|---|
| 5,520,046 A * | 5/1996 | Sornein | E21B 49/08 166/264 |
| 5,889,217 A * | 3/1999 | Rossabi | E02D 1/025 73/864.74 |
| 6,840,121 B2 * | 1/2005 | Thomas | G01N 1/14 73/863.31 |
| 7,662,618 B2 * | 2/2010 | Halden | B01L 3/502 166/107 |
| 8,051,727 B1 * | 11/2011 | Murphy | G01N 1/10 73/864.74 |
| 8,338,182 B2 * | 12/2012 | Halden | G01N 1/16 204/194 |
| 8,578,797 B2 * | 11/2013 | Zeng | E02D 1/06 73/863.23 |
| 2002/0023479 A1 * | 2/2002 | Burge | G01N 33/18 73/1.01 |
| 2003/0004474 A1 | 1/2003 | Barker | |
| 2004/0089079 A1 * | 5/2004 | Engebretson | E21B 49/08 73/863.23 |
| 2004/0180334 A1 * | 9/2004 | Halden | B01L 3/502 435/5 |
| 2005/0218082 A1 | 10/2005 | Williamson et al. | |
| 2007/0161076 A1 | 7/2007 | Halden | |
| 2012/0091067 A1 * | 4/2012 | Taylor | C12Q 1/24 210/740 |

OTHER PUBLICATIONS

PCT/US2012/033912, International Search Report, Nov. 14, 2012.
PCT/US2012/033912, Written Opinion of the International Searching Authority, Nov. 14, 2012.

* cited by examiner

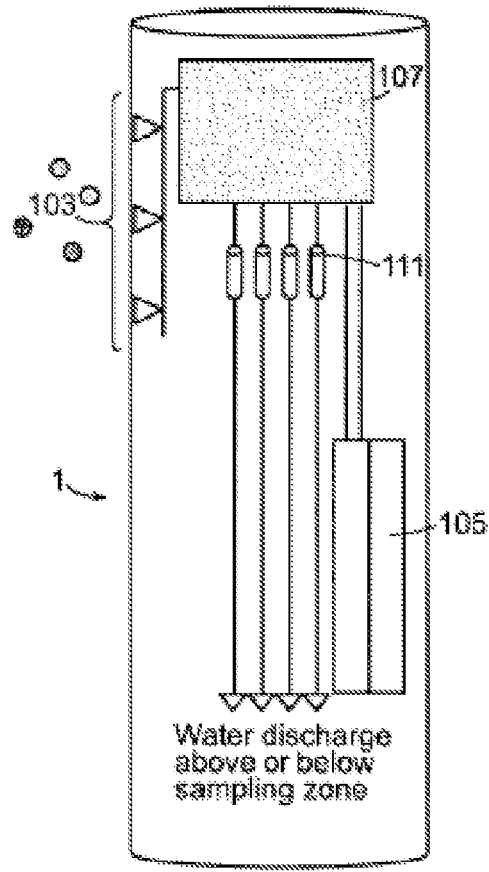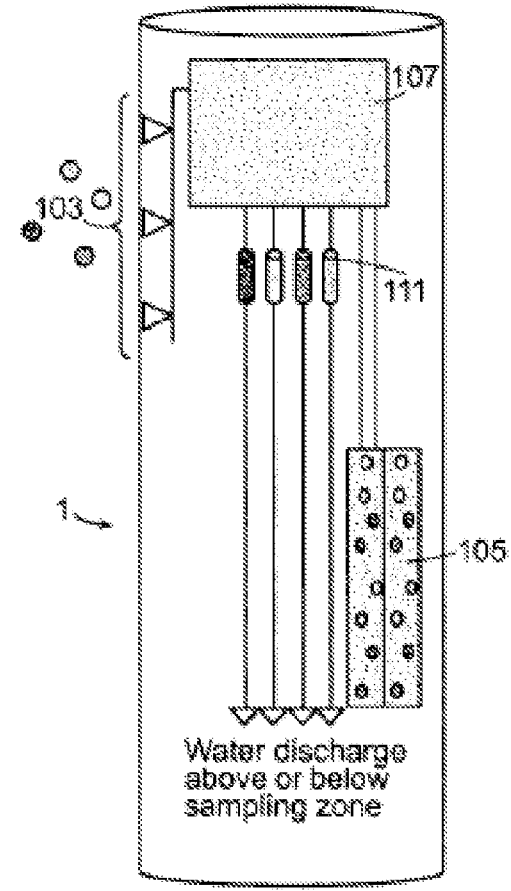
FIG. 1A
(PRIOR ART)
FIG. 1B
(PRIOR ART)

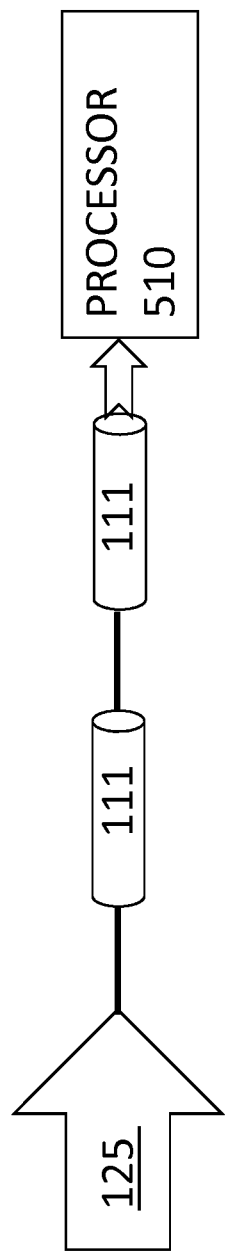

DEVICES AND METHODS FOR DETERMINATION OF BIOAVAILABILITY OF POLLUTANTS

CROSS-REFERENCE TO RELATED APPLICATIONS

Related technology is disclosed in pending PCT patent application publication WO/2009/105241, published on Aug. 27, 2009, and entitled "Methods and Systems for Ground and Surface Water Sampling and Analysis," pending PCT patent application publication WO 2011/140270 published on Nov. 10, 2011, and entitled "Methods and Systems for Ultra-Trace Analysis of Liquids," and U.S. patent application Ser. No. 12/702,033, filed on Feb. 8, 2010, now U.S. Pat. No. 8,338,182, entitled "Methods and Systems for Fluid Examination and Remediation," (herein referred to as the related patent applications) both to a co-inventor of the present application, Rolf Halden, of which the entire contents of each are incorporated herein by reference in their entirety.

Related technology is also disclosed in U.S. Pat. No. 7,662,618 issued on Feb. 16, 2010, entitled "Method and Apparatus for Environmental Monitoring and Bioprospecting," a US patent application having publication number 2007/0161076, published Jul. 12, 2007, entitled "Methods and Systems for Sampling, Screening, and Diagnosis," and a US patent application having publication number 2010/0159502, published on Jun. 24, 2010, entitled "Method and Apparatus for Environmental Monitoring and Bioprospecting," of which the entire contents of each are incorporated herein by reference in their entirety.

STATEMENT REGARDING US FEDERALLY SPONSORED RESEARCH OR DEVELOPMENT

This invention was made with Government support under grant numbers R01 ES015445 and R01 ES020889 awarded by the National Institutes of Health. The Government has certain rights in the invention.

TECHNICAL FIELD

The present invention relates to a method for contaminant sample collection in aquatic or saturated sedimentary environments and to a method for enabling the determination of kinetic rates within a fluid of interest. More particularly, the invention relates to a method for the acquisition of samples that accurately represent the bioavailability of pollutants in aquatic and water saturated sedimentary environments.

BACKGROUND

Persistent contaminants may be present in very low environmental concentrations and yet exert considerable effects on living organisms through the phenomenon of bioaccumulation. Current sample collection, preparation, and analysis practices in environmental engineering that characterize the bioavailability of such compounds may underestimate or overestimate the actual concentrations affecting aquatic or sedimentary biota exposed to such compounds.

Contamination of U.S. surface water sediments is a daunting problem requiring novel solutions for monitoring and remediation. According to the U.S. Environmental Protection Agency (EPA), some 1.2 billion cubic yards of U.S. surficial water sediments (i.e., as found in the top 5 cm of the water surface) are contaminated with toxic pollutants to a degree that poses potential risks to fish as well as to fish-consuming wildlife and humans. Whereas the presence of contaminants in sediments warrants investigation to protect ecosystems and public health, it has long been appreciated that sediment pollution does not necessarily pose a risk that is directly proportional to the mass of contaminants present. Instead, the bioavailability of the pollutants is key information that needs to be known to inform risk assessments for potential human health impacts.

The need for bioavailability data has triggered a renewed interest in the development of novel sampling strategies for the determination of truly dissolved contaminant mass in both bulk water and pore water. Due to partitioning and sorption of contaminants to sediment constituents, including organic carbon, black carbon and soot, the bioavailable contaminant mass of organic pollutants in the dissolved or easily desorbable state typically is only a small fraction of the total mass of the respective contaminant in sediment (typically determined via extraction at high temperature and/or pressure with aggressive organic solvents).

A number of passive sampling strategies have been introduced to enable convenient and inexpensive determination of contaminant concentrations in sediment pore water and bulk water of polluted aquatic environments. While these systems represent a significant advance in environmental monitoring, they also have a number of limitations. Passive samplers which are based on polyethylene and similar sorbents typically capture only a limited spectrum of contaminants and may require performance reference compounds (PRCs) to produce reliable results. Converting analyte mass on the sampler to units of concentration also can be challenging. They also are fragile and may be subject to biodegradation during in situ incubation.

As disclosed in the applications referenced above, FIGS. 1A and 1B provide a schematic of a prior art device in use. Environmental water enters the device 1 through the water intake zone 103. Water is collected in the optional multi-channel reservoir 105 concomitantly during the time period of sampling if desired, either short or long term. During sampling, the pump 107 is used to apply the sample to the non-aqueous collection matrix cartridges 111 at the appropriate flow rate and to deliver, a split sample to the optional reservoir 105 if desired. The separation process is demonstrated schematically. The reservoir includes spots of four different shades of gray. After passing through the pump and contacting the non-aqueous collection matrix columns 111, each of the columns has turned the same shade of gray as one of the spots, representing that each column binds a specific analyte. As in the previous figure, the water from the columns is discharged either above or below the sampling zone to prevent contamination of the sample. It is understood that some types of non-aqueous collection matrices can bind more than one analyte.

Still referring to the referenced patent applications, FIGS. 2A and 2B provide a schematic of an individual non-aqueous collection matrix column 111 that binds a single analyte. Prior to exposure to the sample, the non-aqueous collection matrix includes multiple empty analyte binding sites 301. After contacting the non-aqueous collection matrix with the sample 303, the analyte 305 that specifically binds the non-aqueous collection matrix is bound to the non-aqueous collection matrix in the column. The analytes or other components of the sample that do not bind the non-aqueous collection matrix 307, passes through the column without binding to the non-aqueous collection matrix.

Still referring to the referenced patent applications, FIGS. 3A and 3B show a prior art sampling device wherein a real time sensor 401 is attached to the non-aqueous collection matrix column 403 to allow for detection of the analyte 405 bound to the column. In the embodiment, the real time sensor is further connected for signal transmission, with wire 407 or wirelessly, to a data logger to record the presence of the analyte bound to the sensor. Data can be sent to the data logger at timed intervals, continuously, upon a certain event such as saturation of the column. In an embodiment, a real time sensor can be used to analyze the liquid and the constituents therein 409 that do not bind to the column. In one embodiment, the liquid and the constituents contained therein 409 also can be diverted to the reservoir 105 for a post-deployment determination of the collection efficiency of the non-aqueous collection matrix cartridges 111.

In environmental studies, it also is desirable to obtain a series of time-discrete samples to enable the calculation of rates, for example, of biotransformation and pollutant destruction. Currently, this requires the acquisition, storage and analysis of multiple fluid samples, analysis results of which can inform the rate determination calculations. Storage of large volumes of fluids can be problematic when space is limited or when the analytes of interest are labile and subject to ready disintegration. The present disclosure provides new and novel solutions to overcome the problems inherent in the art related to storing large volumes of unstable liquids. Here disclosed is a method that enables rate determination without requiring the storage and preservation of multiple fluid samples. Although the referenced patent applications disclose technology that has advanced the art, improvement is needed particularly for measurements carried out in aquatic and saturated sedimentary environments. The present disclosure provides new and novel solutions to overcome the limitations inherent in the art. These apparatuses and methods are suitable to make measurements of bioavailability of pollutants. As such, they enable a determination of whether a given environment is posing risks to humans and other biological species due to pollutants that have accumulated in sediments. This information is critically needed by regulatory agencies overseeing and consulting firms serving potentially responsible parties (PRPs) for environmental pollution.

Additionally, it is important to determine information on the kinetics of reactions and processes of interest to address the growing public concern about environmental contamination and its impact on health, agriculture, water supplies and other detrimental effects in the U.S. and around the world. As a result, it is becoming increasing important to demonstrate the effectiveness of environmental remediation processes, even long after a particular remediation site may have been shut down, for example. It is desirable that measurements provide accurate proof of long-term effects and not just discrete time samples (a.k.a. grab samples) or time-average samples, which may or may not be acceptable as reliable evidence of effectiveness in a legal setting, for example.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a method for contaminant mass collection in saturated sedimentary environments for bioavailability determination is disclosed. The method includes securing a casing including a screen to a shell to form an in situ device, where the casing provides a permeable interface between the environment that is subject to sampling and the shell and where the casing and shell hold a water intake zone, at least one pump, sorptive media, and wherein the water intake zone, the at least one pump, the screen and the sorptive media, are all operably linked in sequence, and the screen is in fluid communication with the water intake zone so as to exclude sediments and aquatic life of a size predetermined by the pores of the screen and endemic to the selected environment. The in situ device is deployed in the selected environment, wherein the selected environment includes a saturated sedimentary environment. The pump operates to concentrate analytes from the selected environment in the sorptive media, where the concentrated analytes include the analyte mass of time-weighted fluid samples.

In one aspect the pump comprises a multi-channel pump.

In one aspect the at least one channel comprises at least two extraction cartridges in series containing the same sorptive media.

In one aspect deploying the in situ device includes vertically deploying the in situ device.

In another aspect vertically deploying the in situ device comprises direct-push deployment or augering.

In yet another aspect, the method further includes filtering the water intake to exclude colloidal particles larger than transported or dissolved species in the selected environment.

In yet another aspect, the sorptive media is selected (ii) to simulate uptake of pollutants into biological organisms or (iii) for optimal collector efficiency, including concentration of contaminants that exist in concentration levels below the detection limits of conventional laboratory methods for competitive sample volumes.

In yet another aspect, the method includes operating the pump to concentrate analytes to collect depth-discrete samples from pore water in saturated sediments in situ.

In yet another aspect, the method includes time-averaged collection of said samples over arbitrary periods of time, and analysis of transport phenomena (e.g., dissolved vs. particulate).

In yet another aspect, deploying the in situ device comprises placing the in situ device in a sediment, keeping it buried in the sediment until the interstitial water between the mesh and the casing of the in situ device is in equilibrium with the pore water of the sediment, and activating the pump to pass the water through the sorptive media.

In yet another aspect, the method includes operating the pump continuously at flow rate so that withdrawn water is replaced in the interstitial volume by pore water from the sediment.

In yet another aspect, the method includes operating the pump intermittently so as to pass the entire volume of the interstitial water through the extraction cartridges.

In yet another aspect, the method includes using a piece of tubing running from the in situ device up to the bulk water to enable replacement of the withdrawn volume of water.

In yet another aspect, the concentrated analytes include a concentration of pollutants that sediment-dwelling biota are exposed to.

In yet another aspect, the method includes collecting bulk water concentrations.

In yet another aspect, the method includes measuring a contaminant ratio of bulk water to pore water.

In yet another aspect, the method includes determining of pollutant concentrations in pore water and pollutant concentrations in bulk water combined with analyzing of resident, sediment dwelling biota (e.g., worm) and resident bulk-water dwelling biota; and calculating approximate pollutant concentrations in biota living in sediment and bulk water, respectively.

In yet another aspect, the method includes predicting a level of exposure for organisms that are in contact with both bulk water and sediment pore water by computing an additional bioaccumulation factor to predict their level of exposure and body burden.

In yet another aspect, the at least one pump comprises a multi-channel pump.

In yet another aspect, pore water taken into the in situ device is fractionated into (i) unfiltered pore water, (ii) filtered pore water, and (iii) ultra-filtered, colloid-depleted pore water.

In yet another aspect, parallel selected extraction resins are used in parallel to extract contaminant groups including ionic, non-ionic and differing hydrophobic properties.

In yet another aspect, the method includes elution of the extracted contaminant groups followed by toxicity assays.

Also disclosed is a device for contaminant mass collection in saturated sedimentary environments for bioavailability determination including a casing comprising a water intake zone wherein the casing encloses, a pump, and sorptive media, wherein the water intake zone, the pump, and the sorptive media, are all operably linked in sequence; and a screen providing an interface between the device and the environment.

In one aspect the screen includes a mesh sleeve encasing a cage, the mesh sleeve being in fluid communication with the water intake zone, the mesh sleeve having a mesh size selected to exclude sediments and aquatic life endemic to the environment.

In one aspect the in situ device includes a cone or auger attached to one end of the device.

In another aspect, the in situ device further includes a plurality of filters proximate to the water intake and sized to exclude colloidal particles, where the colloidal particles are larger than transported or dissolved species in the environment in which the device is deployed.

In another aspect the in situ device screen has an entrance closed by a solid or mesh lid.

In one example of the invention, a method for enabling the determination of kinetic rates within a fluid of interest is disclosed including directing fluid flow exiting a test bed to a multi-port switching valve;

controlling the multi-port switching valve to switch the fluid to each of a plurality of channels for a selected time duration;

connecting each of the plurality of channels to at least one in-flow extraction cartridge;

concentrating analytes of interest from the fluid flow;

capturing the analytes of interest on at least one extraction medium; and determining rates by (i) sequentially channeling the fluid through the extraction flow paths, (ii) retrieving the charged extraction cartridges, (iii) analyzing the extraction cartridges, and computing the kinetic rate of interest.

In another example of the invention, analytes are trapped on the extraction media and the fluid, depleted of the analytes of interest, is emptied into the environment, a temporary holding bladder, or individual effluent bags.

In another example of the invention, the kinetic rate of interest comprises the slope of a straight line on a linear or log-linear data plot.

In another example of the invention, the at least one in-flow extraction cartridge comprises a plurality of extraction media that can be arranged in parallel or in sequence.

Another example of the invention further comprises (i) preserving of labile analytes of interest on extraction media for stabilization, (ii) determination of kinetic rates of interest, and does so (iii) without requiring retrieval and analysis of the fluid flow subsamples.

In another example of the invention a system for enabling the determination of kinetic rates within a fluid of interest comprising:

a conduit for directing fluid flow exiting a test bed to a multi-port switching valve;

a controller coupled to the multi-port switching valve to control switching the fluid to each of a plurality of channels for a selected time duration;

wherein each of the plurality of channels is coupled to at least one in-flow extraction cartridge having at least one extraction medium for concentrating analytes of interest from the fluid flow to capture the analytes of interest on the at least one extraction medium; and a processor for determining rates by (i) sequentially channeling the fluid through the extraction flow paths, (ii) retrieving the charged extraction cartridges, (iii) analyzing the extraction cartridges, and computing the kinetic rate of interest.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIGS. 1A and 1B are schematics illustrating the collection of time integrated samples in a groundwater monitoring well and concomitant concentration of various analytes in multiple sampling collectors of the prior art.

featuring a cage or frame added to an IS2 device for deployment of in an aquatic or sedimentary environment.

Figures 5A, 5B, 5C, 5D, 5E:
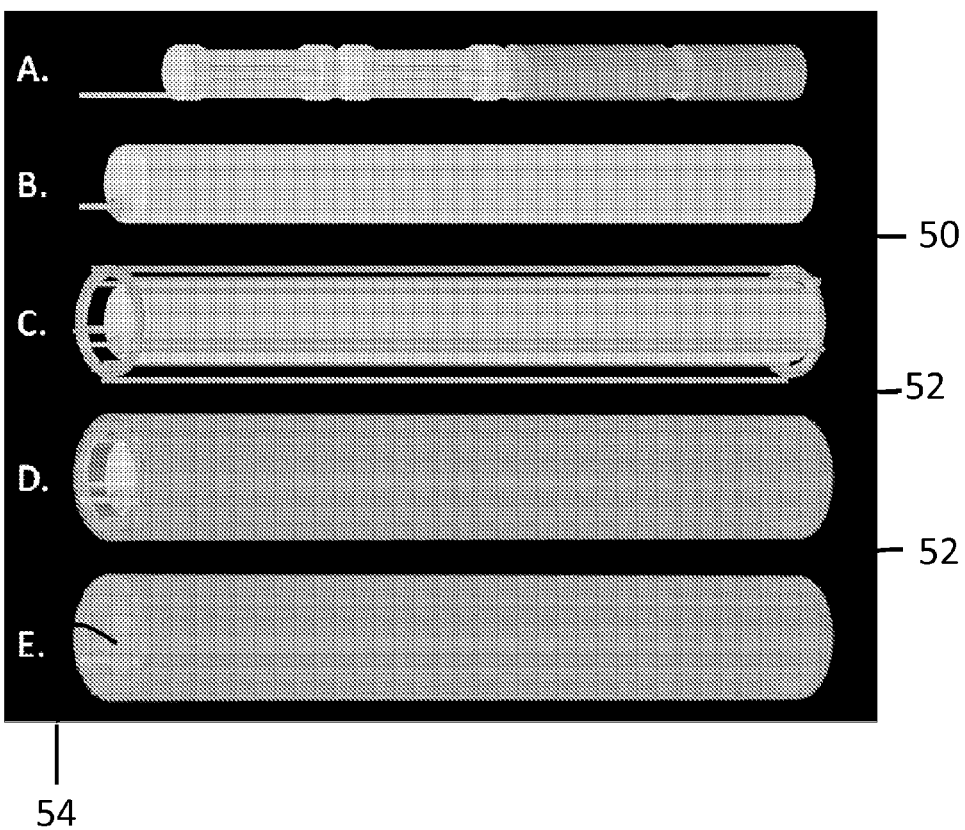
FIG. 5A schematically shows an example of a typical embodiment of the inner workings of a device constructed along the principles disclosed in the related patent applications referenced hereinabove (an "IS2 device"), in which liquid is drawn in through an aperture or tube by a pump and pass through sorptive media cartridges in series and/or parallel.
FIG. 5B schematically shows a further example of a typical embodiment of an IS2 device enclosed in its deployment shell.
FIG. 5C schematically shows an example of a novel in situ sampling device of the present disclosure which is based on a modification of the IS2 device (an "ISB2 device")

FIG. 5D schematically shows an example of a novel ISB2 device is shown featuring a mesh sleeve in which it is inserted.

FIG. 5E schematically shows an example of an operable IS2B device is shown, framed and enclosed in a mesh sleeve, for deployment in an aquatic or sedimentary environment.

Figure 6:
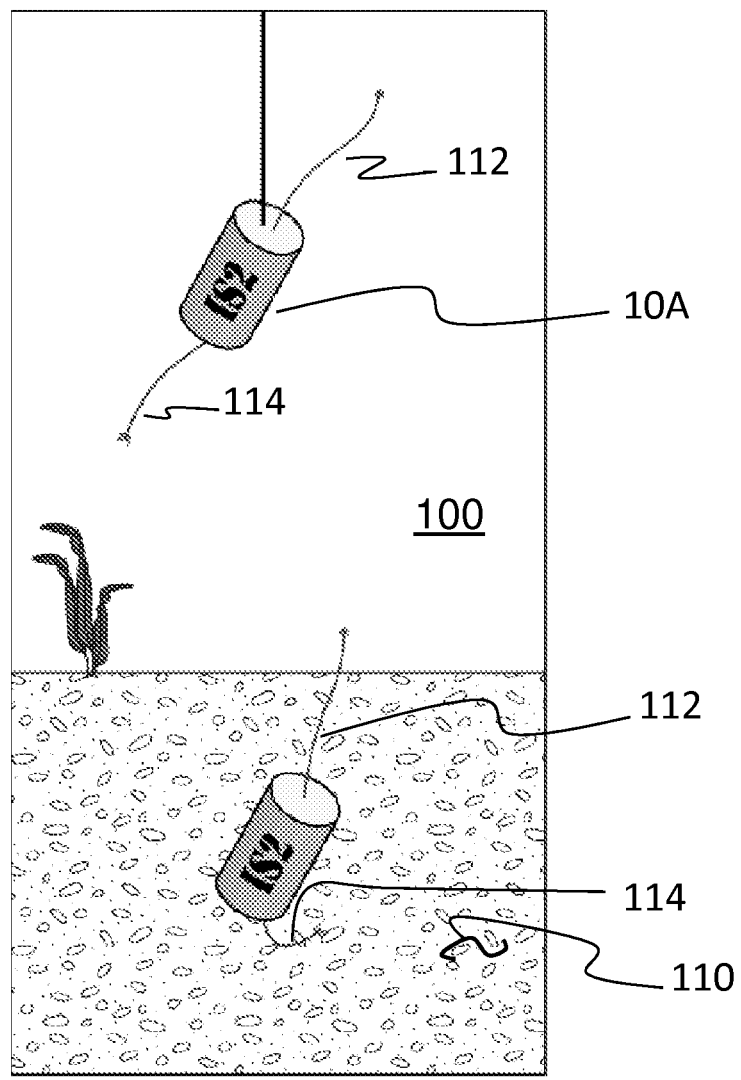

FIG. 6 schematically shows an example deployment of a novel modified IS2 device in a saturated sediment.

Figure 7A:
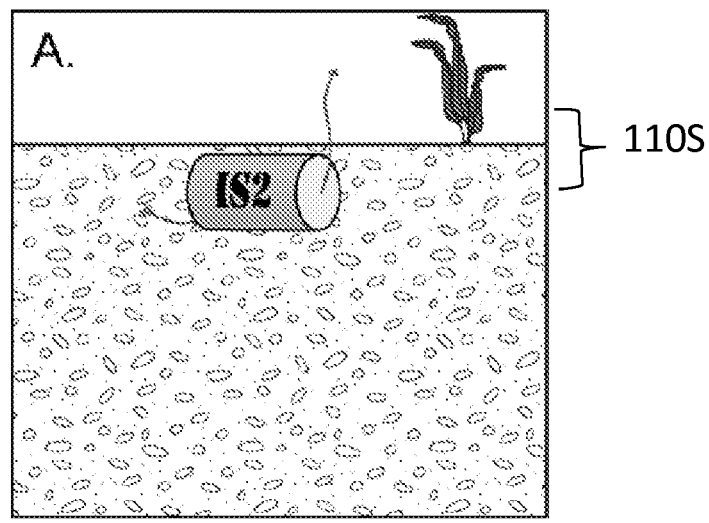

FIG. 7A schematically shows an example of horizontal deployment of a modified IS2 device in a saturated sediment.

Figure 7B:
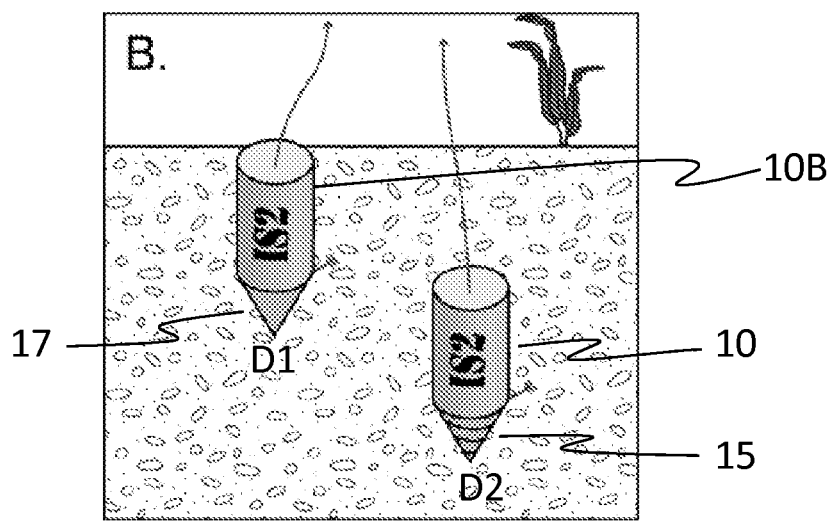

FIG. 7B schematically shows an example of vertical deployment by direct push or by augering in a saturated sediment.

FIG. 8 schematically shows an example of cartridges coupled in series as used in one example embodiment.

Figure 9:
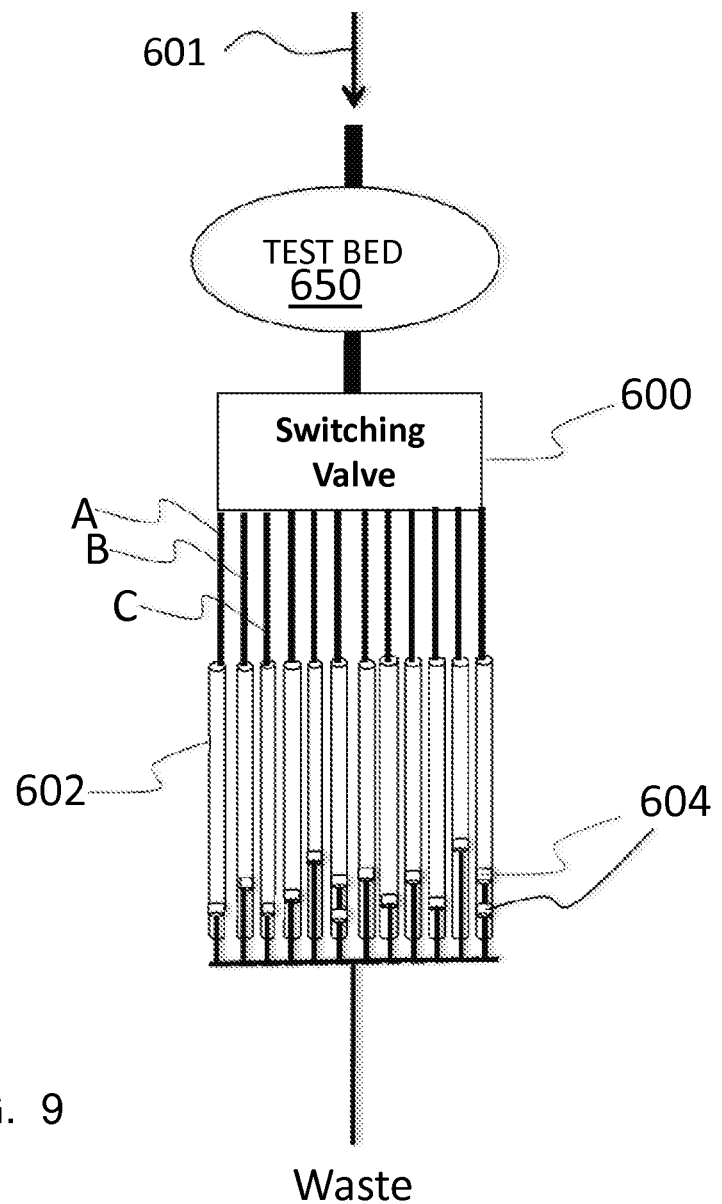

FIG. 9 schematically shows an example of a method for enabling the determination of kinetic rates within a fluid of interest without requiring storage and analysis of said liquid.

Figure 10:
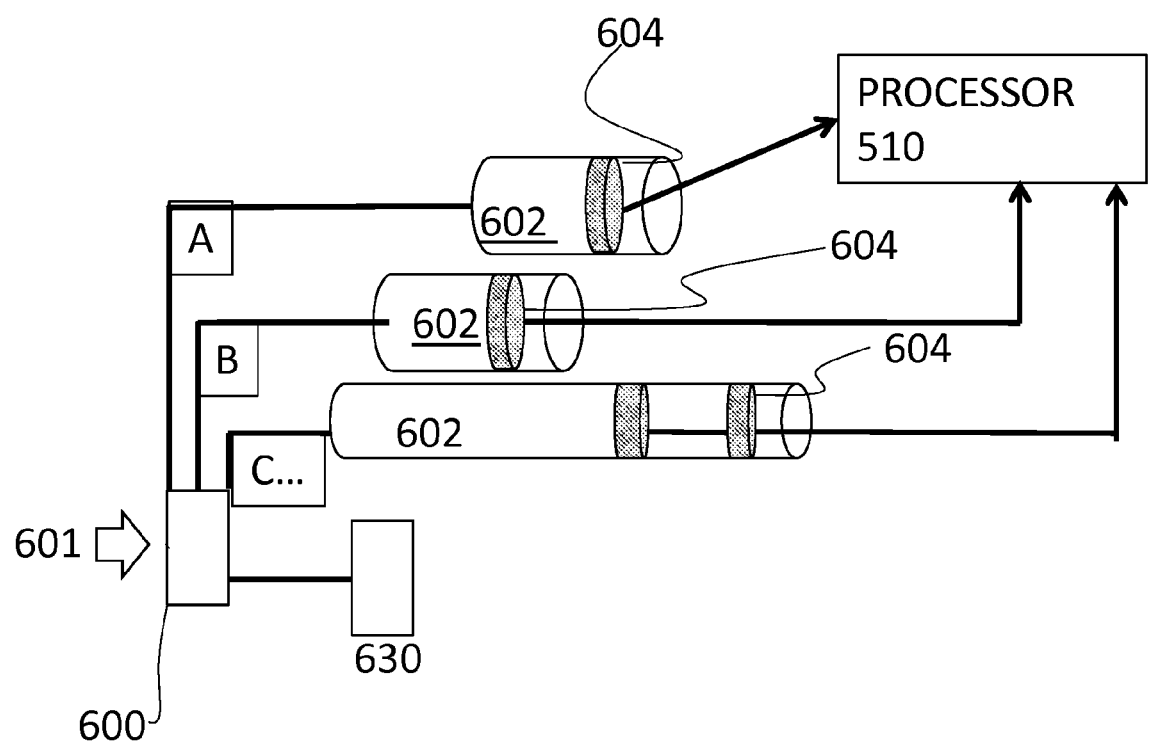

FIG. 10 schematically shows an example of system for enabling the determination of kinetic rates within a fluid of interest.

Figure 11:
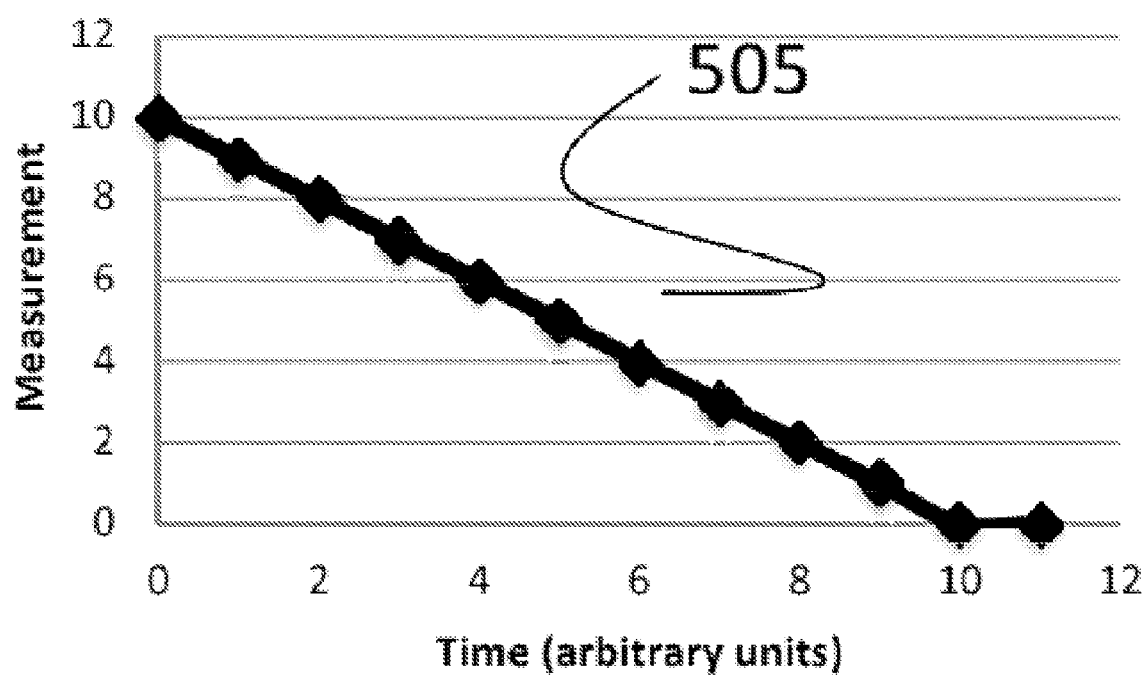

FIG. 11 schematically shows an example of data analysis for the determination of kinetic rates within a fluid of interest.

Figure 12:
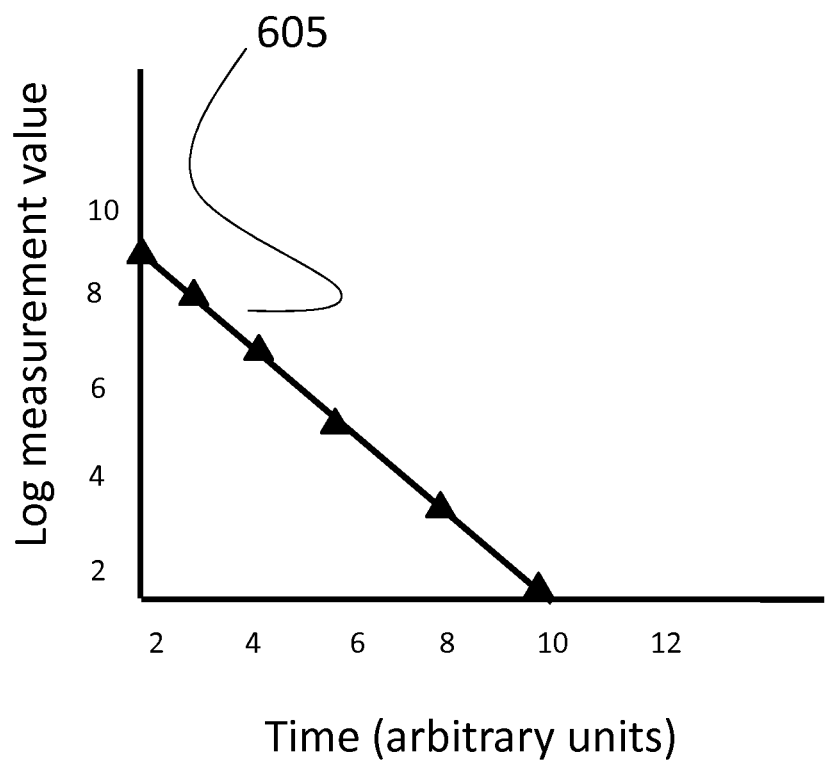

FIG. 12 represents a hypothetical example of data analysis for the determination of kinetic rates in a logarithmic plot for assessing first-order rate kinetics.

Figure 13:
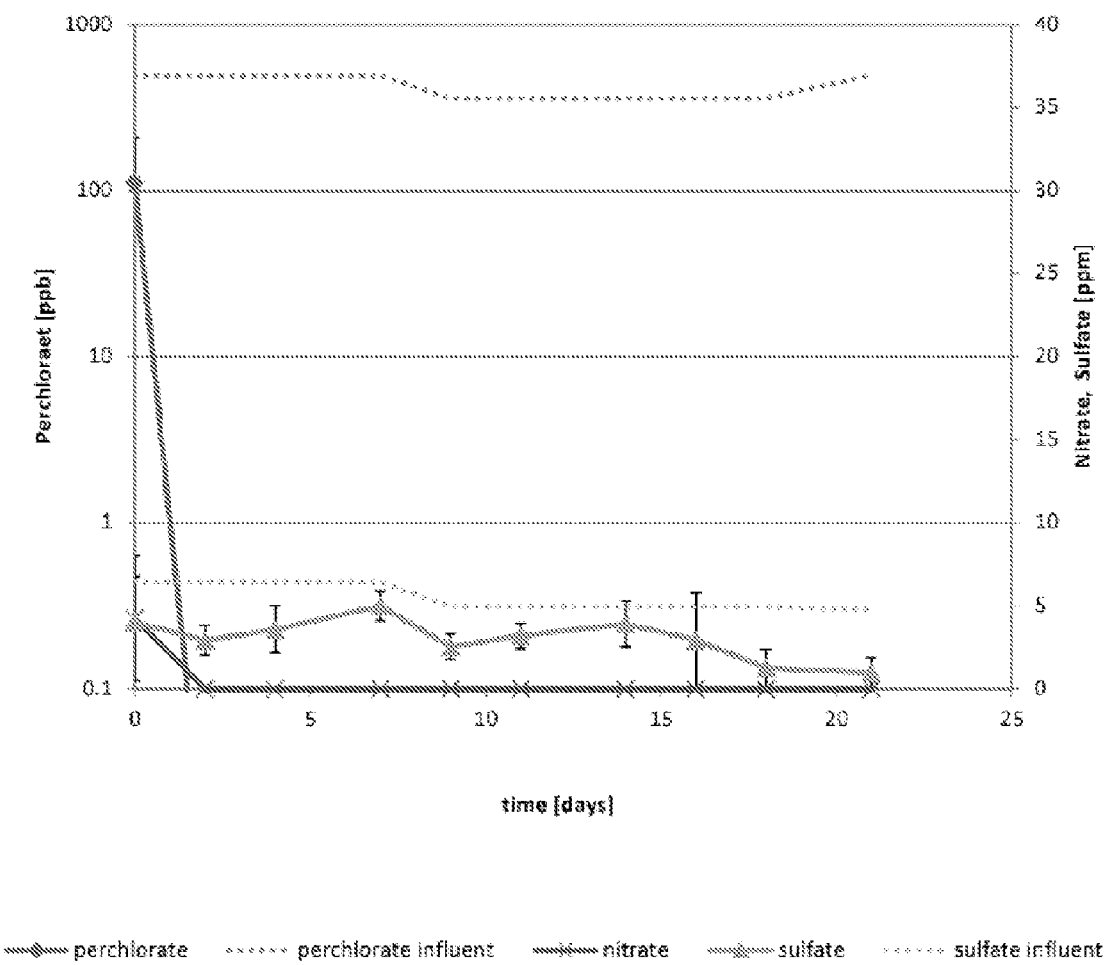

FIG. 13 represents an example of experimental results for time discrete monitoring of perchlorate and nitrate containing liquids reflective of an industrial site to which sodium acetate (Na acetate) was added to effect biologically mediated contaminant removal.

Figure 14:
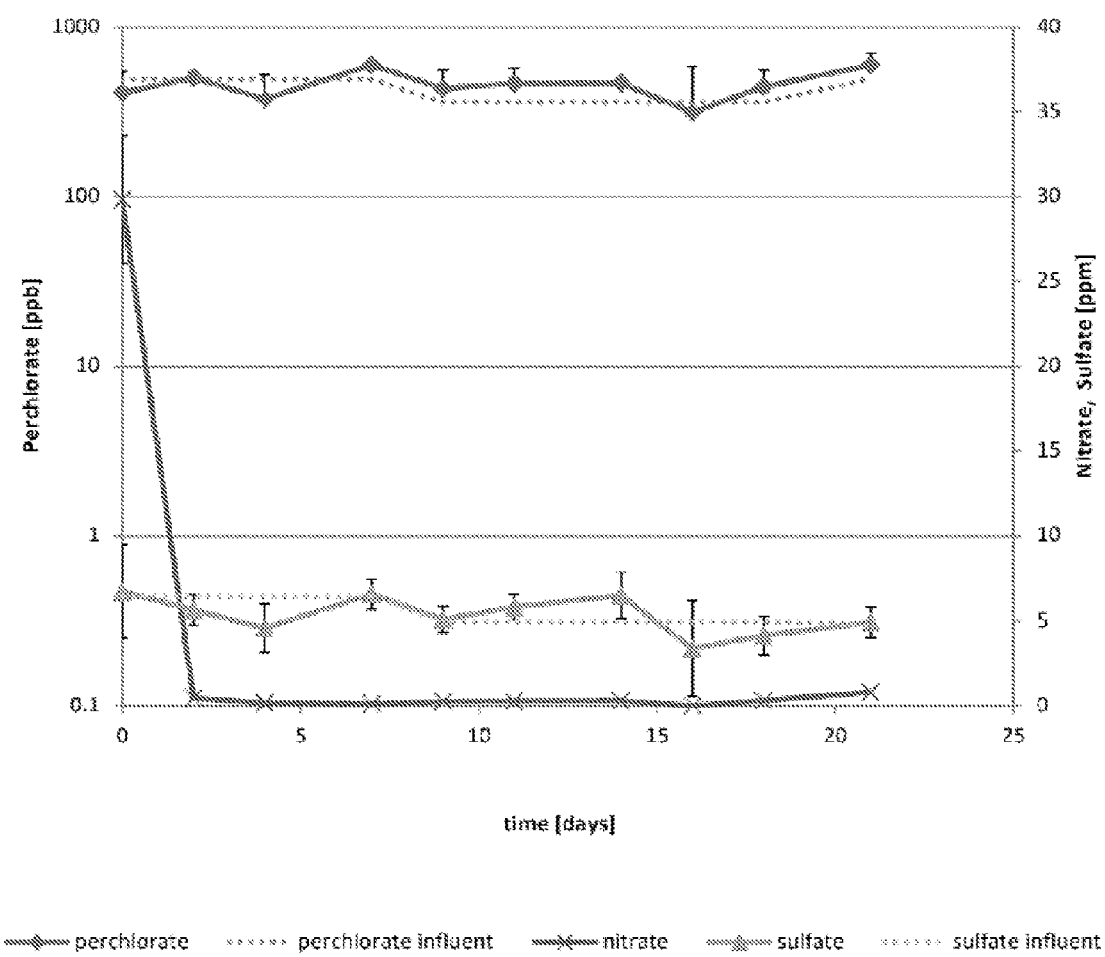

FIG. 14 represents an example of experimental laboratory results substantially replicating time discrete monitoring of monitored natural attenuation (MNA) from an industrial site.

Figure 15:
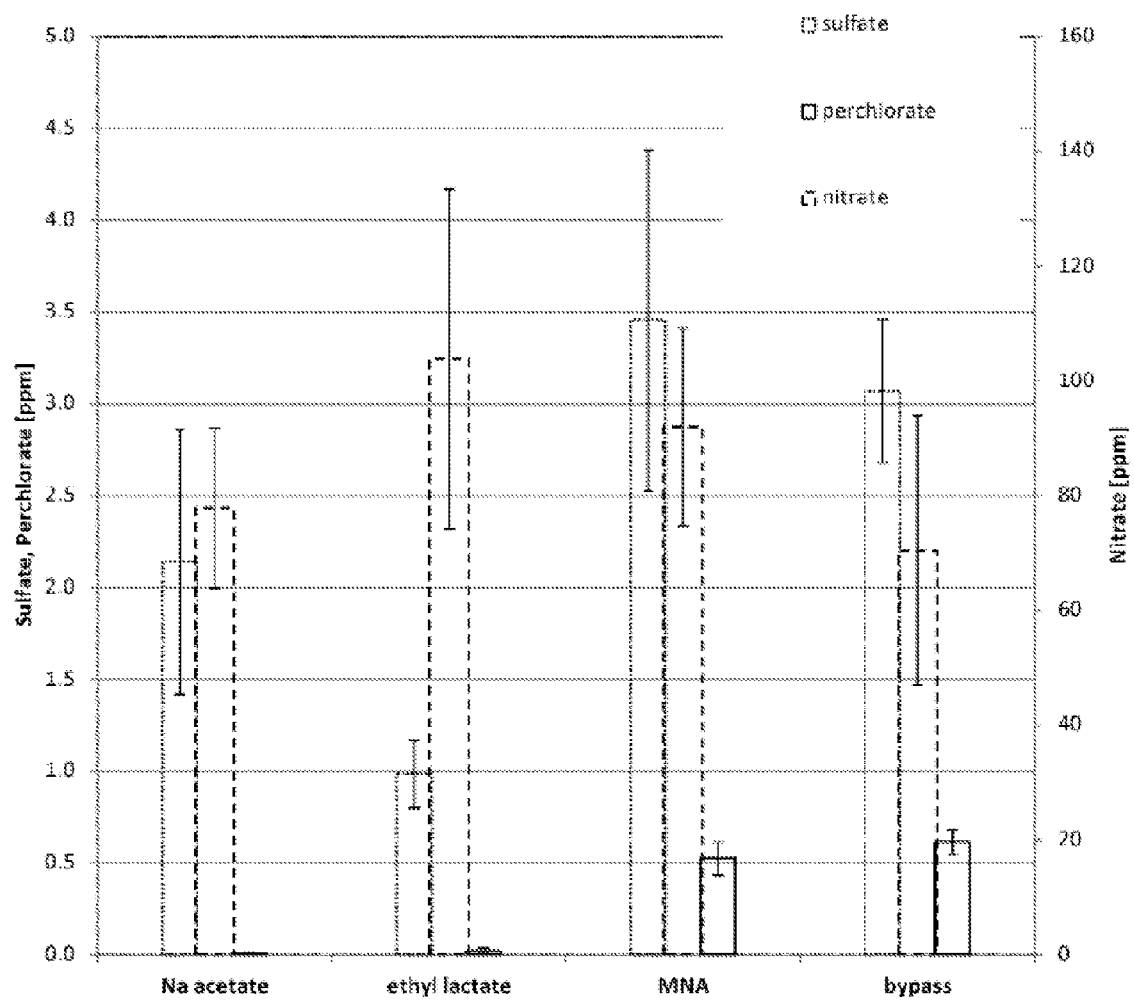

FIG. 15 represents an example of experimental laboratory results substantially replicating composite effluent analysis of effluents of microcosms reflective of an industrial site.

Figure 16:
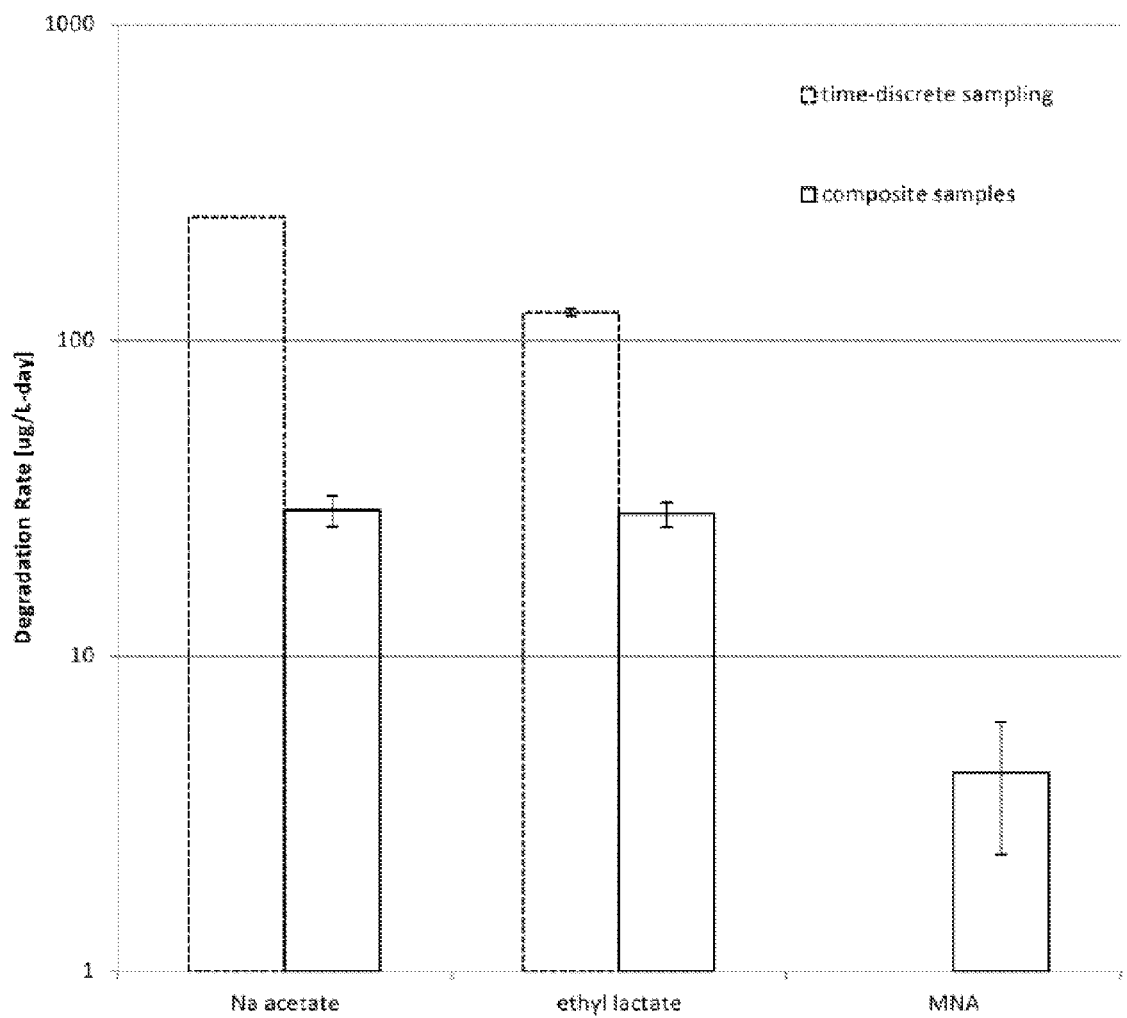

FIG. 16 represents an example of experimental laboratory results substantially comparing the process of rate determination for an industrial site using time discrete sampling versus composite sampling.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for contaminant mass collection in saturated sedimentary environments for bioavailability determination and for enabling the determination of kinetic rates within a fluid of interest. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to analysis of environmental conditions. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of contaminant sample collection in aquatic or saturated sedimentary environments:

"Aquatic environment" has its generally accepted meaning and is intended to include an environmental compartment occupied by a fluid, such as a bulk liquid or bulk water.

"Saturated sedimentary environment" has its generally accepted meaning and is intended to include an environmental compartment occupied by a mixture consisting of at least one fluid and at least one solid, for example, a heterogeneous mixture of liquids and solids such as sediment of a surface water (e.g., a lake) containing sediment and tissue from biota.

"IS2 system or IS2 device" means a device constructed along the principles disclosed in the related patent applications referenced hereinabove.

"IS2B system or IS2B device" means the new and novel in situ sampling device of the present disclosure that is based on a modification of the IS2 device.

"Analyte" is understood as any compound that may be present in a sample that can be captured using a non-aqueous collection matrix and detected using an assay or method.

By "cartridge" is meant a container enclosing the solid matrix through which the sample is passed through or over. The solid matrix is enclosed in the cartridge to allow the sample to pass through the cartridge, for example into an inlet port and out of an outlet port, wherein the solid matrix is retained within the cartridge.

By "concentration" or "concentration of the analyte" as used herein is understood as decreasing the volume in which a given mass of an analyte is present. For example, decrease the volume in which the given mass analyte is present by at least at least 2-fold, at least 10-fold, at least 102-fold, at least 103-fold, at least 104-fold, or at least 105-fold.

"Contacting" as used herein is understood as bringing two components into sufficient proximity (e.g., a groundwater sample containing or potentially containing an analyte and a non-aqueous collection matrix that can bind the analyte, a fluid sample and the water intake zone of the device) for sufficient time and under appropriate condition of temperature, pressure, pH, ionic strength, etc. to allow for the interaction of the two components, e.g., the binding of the analyte to the non-aqueous collection matrix, the entry of water into the device through the water intake zone. Contacting in the context of the invention typically occurs in a non-aqueous collection matrix container such as cartridge, column, or other device that allows the water to flow through the container in a path to allow the water to contact the non-aqueous collection matrix. Contacting a non-aqueous collection matrix cartridge is understood as contacting the matrix within the cartridge with the fluid sample.

"Control system" as used herein is understood as a device such as a computer or recording device. The control system can be used predominantly for mechanical uses, such as positioning the device in the well. The control system can also be used for turning on and off various components of the device, such as the pump, opening and closing fluid lines in the pump, directing collection of a time integrated or time discrete sample, etc. The control system can also be used for the purpose of data collection in the form of electronic data, or by attachment to a chart recording device. The control system can be physically attached to the device by wires or cables. Alternatively, a wireless control system can be used with the device.

As used herein, "detecting", "detection" and the like are understood as an assay or method performed for identification of a specific analyte in a sample. The amount of analyte detected in the sample can be none (zero) or below the limit of detection (<LOD), positive and within the calibrated range, or positive and outside of the calibrated range of the assay or method.

"Distal" is understood herein as meaning further away than, typically relative to the device of the invention. For example, a waste line that empties distal to an inflatable liner empties on the far side, i.e., the opposite side, of the liner when viewed from the device. The side of the inflatable liner facing the device would be "proximal" to the device.

"Dry sample" as used herein is understood as the non-aqueous collection matrix cartridge after it has made contact with a fluid sample, such as groundwater or surface water, wherein at least one analyte is suspected of or known to be bound to the non-aqueous collection matrix in the cartridge. A dry sample can contain water or other fluid. All moisture does not need to be evacuated from the cartridge. However, the sample contains no more fluid that will fit in the cartridge with the non-aqueous collection matrix present in the cartridge. Both time-discrete samples and time-integrated samples can be converted to dry samples by use of a non-aqueous collection matrix cartridge. Conversion of aqueous to dry samples may occur in the subsurface (i.e., in situ) or on-site prior to shipping of samples.

"In situ" as used herein is understood as in the subsurface, preferably at or near the site that the sample is collected. "At or near the site that the sample is collected" is understood as at the same or similar depth such that pressure changes have little or no effect on the sample from the time that the sample is collected to the time that the sample is contacted with the non-aqueous matrix. It is understood that lateral movement within the well will typically have far less effect on pressure in the sample than movement in the depth in the well. In situ contacting of samples with a non-aqueous matrix is differentiated from contacting the non-aqueous matrix with the sample at the surface (i.e., ground level) when the sample is collected in the subsurface. It is understood that contacting surface water with the non-aqueous matrix at the site of collection (i.e., at ground level) is understood as contacting the sample with the matrix in situ.

As used herein, "interchangeable" is understood as the device being designed so that one or more components of the device can be readily exchanged for a similar component. For example, lines and non-aqueous collection matrix cartridges can be joined using bayonet connectors, rapid release connectors, quick connectors, screw connectors, compression connectors, Luer lock, or other similar type connectors that require no tools for the separation or connection of components. Further, non-aqueous collection matrix cartridges can be exchanged depending on the site of groundwater to be tested, the type and quantity of analyte to be detected, and the quantity of water to be tested. Similarly, tubing or other connectors for example from the pump to the non-aqueous collection matrix cartridges may be changed depending on the analyte to be detected to prevent adsorption into the tubing, or the volume or flow rate of the water to be tested. Interchangeable parts such as tubing or cartridges can be disposable. Such considerations are well understood by those of skill in the art.

As used herein, "in vivo microcosm array" (IVMA) is understood to include a sampler or testing device as shown in FIG. 9-10, its principal components include: a test bed 650 in fluid communication with a multi-port switching valve 600. The multi-port switching valve 600 is controlled to switch the fluid to a plurality of channels A, B, C etc., wherein the plurality of channels includes at least two channels. Each of the plurality of channels is connected to at least one in-flow extraction cartridge 602. Analytes of interest from the fluid flow are concentrated in the at least one in-flow extraction cartridge 602. The at least one in-flow extraction cartridge 602 may advantageously contain at least one extraction medium 604 for capturing the analytes of interest. IVMAs may preferably be miniaturized for in vivo applications, such as, for example, implanting to or affixing on the body of a living organism.

As used herein, "non-aqueous analyte collection matrix", "matrix", "resin", and the like are understood as material or a mixture of materials that are designed to come into contact with the fluid sample and, through their relatively greater affinity relative to water, will remove and concentrate the analyte or analytes of interest from the fluid sample including dissolved solid, gas, and particulate materials of interest. For example, groundwater or surface water can be passed through, over, or mixed (i.e., contacted) with the non-aqueous analyte collection matrix, thereby causing this matrix to bind and concentrate one or more analytes. It is understood that the binding properties of the materials for one or more specific analytes can depend on various properties of the sampled fluid, for example, ionic strength, pH, etc. The material can bind the analyte(s) specifically, e.g., the chelator EDTA for binding of heavy metals, peptide metal binding motifs, antibodies for binding desired antigens, molecular pockets formed by molecular imprinting, or specific and nonspecific binding sites relying on van-der-Waals forces, hydrophobic interaction, hydrophilic interaction, mixed-mode interaction, hydrogen bridges, affinity binding sites, etc. Alternatively, the material can bind the analyte(s) based on charge, e.g., cation exchange, anion exchange or mixed-mode ion exchange materials. The analyte collection matrix does not need to be a solid. It can be a non-aqueous liquid, a gel or a semi-solid that attracts and concentrates the analytes by the mechanisms mentioned above as well as by chemical partitioning out of the water and into the analyte collection matrix. The matrix can be contacted with the liquid sample in any known format, including a column, bulk binding, etc. Such methods are well known to those of skill in the art.

"Obtaining" is understood herein as manufacturing, purchasing, or otherwise coming into possession of.

"Operably linked" is understood as a connection, either physical or electronic, between two components of the device, or a component of the device and a remote sensor, data collector, controller, computer, or the like such that the components operate together as desired. For example, a fluid line operably linked to a non-aqueous collection matrix cartridge is understood as a fluid line that delivers fluid to the non-aqueous collection matrix cartridge without loss of fluid and at the desired flow rate. A device operably linked to the controller can be moved to the desired position in the well, and the pump or other components of the device can be turned on or off using the controller.

As used herein, "plurality" is understood to mean more than one. For example, a plurality refers to at least two, three, four, five, ten, 25, 50, 75, 100, or more.

As used herein, "real time" is understood as while the process is occurring, for example, collecting data, and preferably transmitting data to a device or person, at the same time the sample is being collected. The data need not be transmitted instantaneously, but is preferably transmitted within about 1 minute, 2 minutes, 5 minutes, 10 minutes, 15 minutes, or 30 minutes from the time that it was collected, or the collection of the data packet was completed. Data can be sent continuously or periodically in real time for monitoring the progress of a process, or can be sent episodically, e.g., upon overload of a non-aqueous collection matrix cartridge, failure of the device, detection of water table, completion of in well purge, etc.

A "sample" or "fluid sample" as used herein refers to a material, particularly ground water, bulk water, pore water or surface water that is suspected of containing, or known to contain, an analyte. A fluid sample can include dissolved gases, as well as any dissolved or particulate solids. Methods and devices of the invention can be used for the collection of gases as well as dissolved or particulate solids upon selection of the appropriate non-aqueous collection matrix. A reference sample can be a "normal" sample, from a site known to not contain the analyte. A reference sample can also be taken at a "zero time point" prior to contacting the cell with the agent to be tested. A reference sample can also be taken during or after collection of a time integrated sample. A reference sample is typically a time discrete sample when it is collected at the same site as a time integrated sample.

Example Embodiments

Figures 2A, 2B:
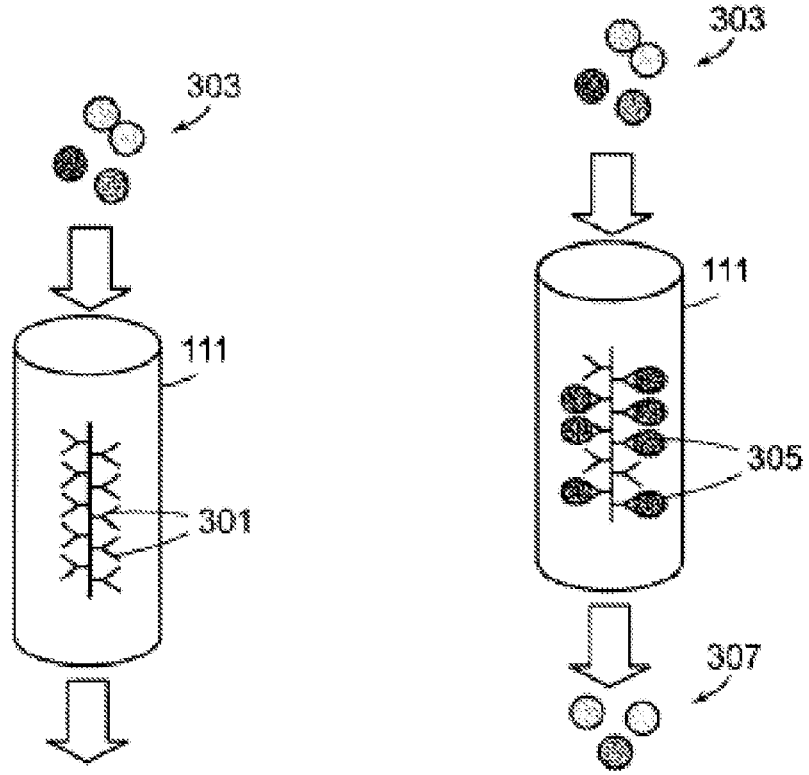
FIGS. 2A and 2B are schematics of a prior art embodiment of the analyte collector showing the concentration of a specific analyte from groundwater over time.
Figures 3A, 3B:
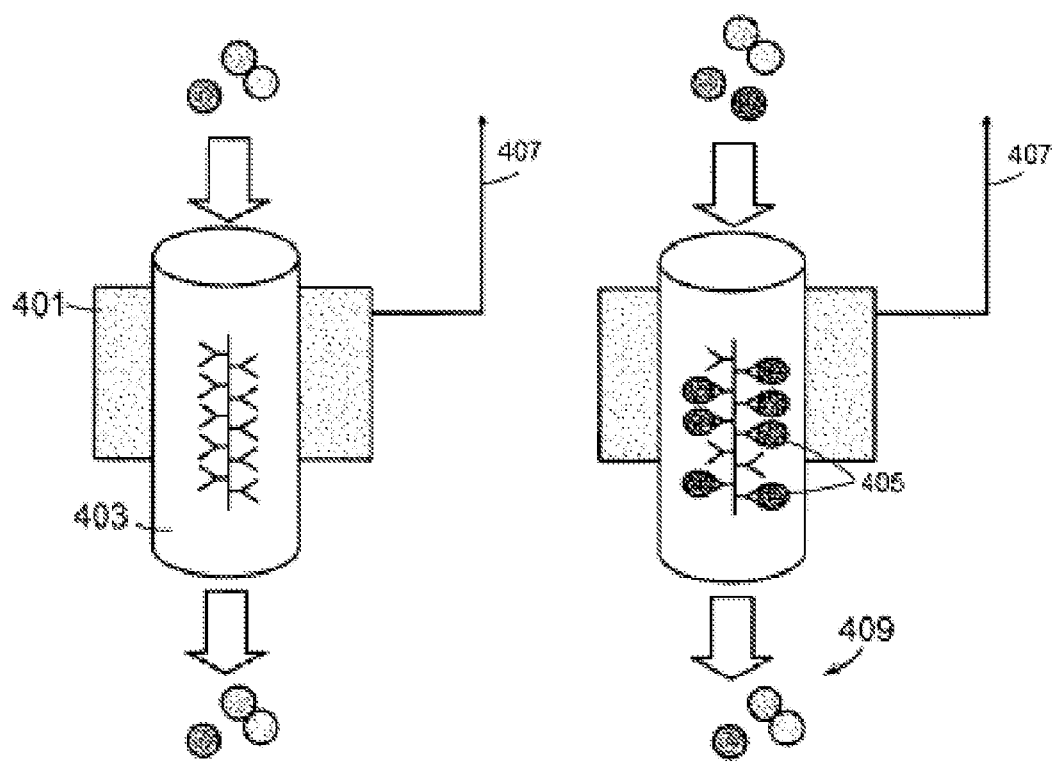
FIGS. 3A and 3B are schematics of a prior art embodiment of the analyte collector equipped with a real-time sensor suitable for in situ detection of analytes concentrated from groundwater.
Figure 4:
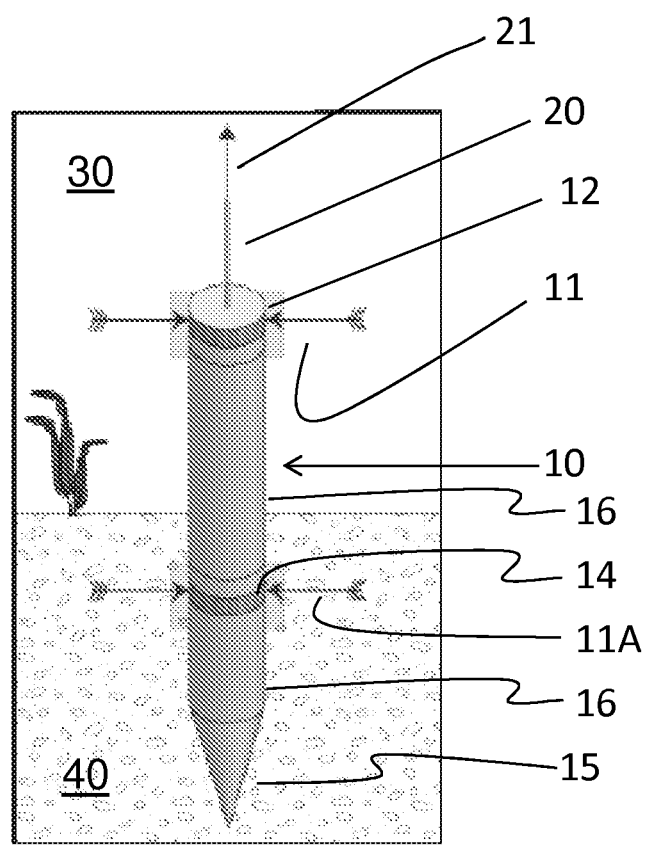
FIG. 4 schematically shows an example of a device deployed in sediment for simultaneous sampling of bulk and pore water at differing flow rates.

Referring now to FIG. 4, an example of a method for the acquisition of samples that accurately represent the bioavailability of pollutants in aquatic and water saturated sedimentary environments. There shown is an in situ sampling device 10 vertically deployed partially in sediment 40, containing pore water, and partially in bulk water 30. The in situ sampling device 10 includes a first intake 12 and a second intake 14 coupled together by casing 16. A cone 15, auger or the like is attached to one end for placement in the sediment 40 or like environments. Flow is indicated by arrows 11, 11A. Both flow rates are controlled by pumps (as shown in FIG. 1A, for example) which are, in turn controlled by a (not shown) controller, such as a personal computer, electronic circuitry, ASIC or the like. The in situ sampling device is coupled to control lines 21 running in or along a tether 20 which is used during placement and removal of the device. The tether 20 and the control lines 21 are optional, as the device in another embodiment also can be operated autonomously with the controls built into the device shell.

In example embodiments the device may advantageously be operated (i) to effect the deployment of sorptive media in aquatic and saturated sedimentary environments, in which said media may be selected (ii) to simulate uptake of pollutants into biological organisms or (iii) for optimal collector efficiency, including concentration of contaminants that exist in concentration levels below the detection limits of conventional laboratory methods for competitive sample volumes.

In further example embodiments the in situ sampling device may advantageously be operated (iv) to collect depth-discrete samples from pore water in saturated sediments in situ, (v) for time-averaged collection of said samples over arbitrary periods of time, and (vi) for analysis of transport phenomena (e.g., dissolved vs. particulate).

Active sampling of water using an electric pump is technically more challenging but can address some of the shortcomings of passive samplers. As referenced in the pending patent applications above, a strategy for obtaining time-averaged concentrations of bulk water was introduced recently by co-inventor Halden in the form of an in situ sampler (herein referred to as the IS2 system). Obtaining time-averaged concentrations of contaminants has the obvious benefit of avoiding measurement bias due to unrepresentative grab sampling. The IS2 system acquires and extracts water in situ during sampler incubation. This makes it very cost effective because only the contaminant-charged solid phase extraction (SPE), cartridge is shipped for analysis instead of large amounts of water. It also enables simultaneous parallel processing of water with and without filtration to determine total, suspended and colloidal contaminant mass. In addition, contaminants immobilized on the SPE cartridges have a longer holding time, which affords the freedom of leaving the samples at room temperature for extended periods of time without measurable loss of analyte mass. The active sampling approach is applicable to a broad range of organic and inorganic contaminants ranging from infinitely water-soluble chemicals (that are captured for example by ion exchange resins) to highly hydrophobic organic pollutants that are captured by molecularly imprinted polymers, activated carbon, $C_{6-18}$ sorbents, and specialized extraction resins, many of which are commercially available.

In the instant in situ device (herein sometimes referred to as IS2B, the advantages of bulk water sampling in the IS2 system are paired with additional benefits for pore water analysis, as disclosed in pending U.S. patent application Ser. No. 12/702,033. By using multi-channel pumps, pore water taken into the IS2B device can be fractionated into (i) unfiltered pore water, (ii) filtered pore water, and (iii) ultra-filtered, colloid-depleted pore water. In addition, parallel use of selected extraction resins enables the selected (targeted) extraction of contaminant groups of (iv) ionic, (v) non-ionic and (vi) differing hydrophobic properties. Elution of these contaminant fractions followed by toxicity assays can inform on the type and identity of unknown toxicants in a process analogous to the Toxicity Identification Evaluation (TIE) approach as described by co-inventor Halden (Editor) in the publication entitled "Contaminants of Emerging Concern: Ecotoxicological and Human Health Considerations." Oxford University Press, New York, N.Y. 620pp. 2010.

In one example embodiment, the in situ method and device informs on sediment contaminants of great ecological and human health significance including organohalide compounds (OHCs), and more particularly, organochlorine pesticides (OCPs) which are persistent hydrophobic contaminants that are ubiquitous in many sediments. These contaminants bioaccumulate in higher predators and can produce a range of toxic responses from lethality to endocrine disruption. Important contaminants found at one proposed IS2B deployment site, Lake Apopka, Fla., include p,p'-DDE and dieldrin, ranking #21 and #17, respectively, on the 2010 CERCLA Priority List of Hazardous Substances. These compounds are present at high levels in soils and in fish in the Lake Apopka/muck farm area as well as at many other sites around the United States. Emerging contaminants also pose significant risks and will be examined here. The hexa-fluorinated insecticide fipronil and its derivatives are known to be persistent, bioaccumulative and toxic. The two antimicrobial compounds triclosan and triclocarban are persistent, bioaccumulative, toxic, and endocrine disrupting contaminants of sediments, surface waters and soils nationwide and also are known or suspected to promote cross-resistance to life-saving antibiotics used in human medicine. In addition, both triclosan and triclocarban have been found to occur in U.S. sediments at concentrations orders of magnitude above those of OCPs. Due to their antimicrobial properties, they are suspected to inhibit microbial activity and biodegradation of EPA priority pollutants, including DDE and dieldrin.

Referring now to FIG. 5A-FIG. 5E, there shown is a partially cut-away view of an example embodiment of the intake of a device for contaminant mass collection in aquatic or saturated sedimentary environments for bioavailability determination. The intake screen shown in FIG. 5A, can be operably linked to an IS2 device to concentrate on solid phase extraction media the analyte mass of time-weighted fluid samples.

As shown in FIG. 5C, the intake of an in situ device is modified for deployment in a body of water or in saturated sediment. A cage 50 is provided that secures the device and provides a permeable interface between the device and the environment.

As shown in FIG. 5D a mesh sleeve 52 encases the cage 50 and provides a route by which water may reach the device, while sediments and aquatic life are excluded. The material and pore size of the mesh may be selected by those skilled in the art as appropriate for local environmental conditions.

Referring now to FIG. 5E, the entrance to the mesh sleeve 52 is closed by a solid or mesh lid 54.

Referring now to FIG. 6, having described the in situ device in detail, the operation of the device will now be described to promote further understanding of the invention. An in situ device 10A may be deployed at any depth in a body of water 100 or may be embedded (i.e., buried) in sediment 110. Influent enters through one tube or aperture and effluent is released distally to prevent short-circuiting.

Referring now to FIG. 7A, there shown in an in situ device deployed horizontally in sediment. When deployed in sediment 110, the in situ device 10A may be deployed horizontally to collect samples from near-surface sediment layers 110S.

Now referring to FIG. 7B, collection from deeper layers D1, D2 may be accomplished though vertical deployment. In vertical deployment, a cone 17 or auger 15 may advantageously be attached to the device, enabling direct-push deployment or augering to any depth. Filters may be included in the in situ device 10 to exclude colloidal particles, enabling the device to discriminate between transported and dissolved species. Influent enters through one tube or aperture and effluent is released distally to prevent short-circuiting.

In this way the device enables (i) the deployment of sorptive media in aquatic and saturated sedimentary environments, in which said media may be selected (ii) to simulate uptake of pollutants into biological organisms or (iii) for optimal collector efficiency, including concentration of contaminants that exist in concentration levels below the detection limits of conventional laboratory methods for competitive sample volumes. Furthermore, this technology enables (iv) the collection of depth-discrete samples from pore water in saturated sediments in situ, (v) time-averaged collection of said samples over arbitrary periods of time, and (vi) analysis of transport phenomena (e.g., dissolved vs. particulate).

Further disclosed are methods for using the IS2B device. In one scenario, the IS2B device is placed in a sediment, kept buried in the sediment until the interstitial water between the mesh and the casing of the device is in equilibrium with the pore water of the sediment, and the integrated pump in the device is then activated to pass the water through the IS2 extraction cartridges. The pump may be operated continuously at a very slow flow rate. During pumping, the withdrawn water is replaced in the interstitial volume by pore water from the sediment. Alternatively, the pump may be operated intermittently to pass the entire volume of the interstitial water through the extraction cartridges. A piece of tubing running from the IS2B device up to the bulk water may serve to enable replacement of the withdrawn volume of water. This process of periodic charging can be repeated once or multiple times to achieve higher pollutant loading on the extraction cartridges and thus lower method detection limits. Use of the IS2B apparatus as described above can inform on the concentration of pollutants that sediment-dwelling biota, such as aquatic worms, are exposed to.

In another approach, the method consists of using the IS2B as described above and collecting bulk water concentrations at the same time with a regular IS2 device. Comparison of the results from both measurements can inform on the contaminant ratio of bulk water to pore water.

In yet another approach, use of the ISB2 device for determination of pollutant concentrations in pore water and the IS2 device for determination of pollutant concentrations in bulk water can be combined with analysis of resident, sediment dwelling biota (e.g., worm) and resident bulk-water dwelling biota (e.g., fish). Once the Biota Sediment Accumulation Factor (BSAF) and the Bioaccumulation Factor (BF) in bulk water have been determined, it is no longer necessary to harvest and sacrifice biological specimens to estimate the concentrations in them. Instead, the concentrations in bulk and pore water are determined conveniently with the IS2 and the ISB2 device, respectively, and the BSAF and BF factors are used to calculate approximate pollutant concentrations in biota living in sediment and bulk water, respectively.

For organisms that are in contact with both bulk water and sediment pore water (e.g., clams), additional BF may be computed to predict their level of exposure and body burden using the IS2 and ISB2 device.

Referring now to FIG. 8, an example of cartridges coupled in series as used in one example embodiment. Fluid flow 125 is coupled a series of at least two in-flow extraction cartridges 111. Each of the cartridges is filled with an extraction medium that scavenges (concentrates) an analyte of interest from the fluid flow passing through it. Analytes are trapped on the extraction media and the fluid, depleted of the analytes of interest, is emptied into the environment, a temporary holding bladder, or individual effluent bags.

In this useful embodiment, capture of the analyte is done by the at least two cartridges 111 coupled together in series. In order to determine whether a single cartridge is overloaded, each of the cartridges in series must contain the same resin or filtering media. The series configuration of cartridges will show complete capture of the analyte through determination of breakthrough behavior in the first cartridge to receive the flow. That is, if the first cartridge is oversaturated resulting in breakthrough of the analyte of interest, the second cartridge will capture the rest of the analyte. Presence of the analyte in the front extraction cartridge and absence of the analyte in the second (or third, fourth, etc.) cartridge, indicates that the mass of the analyte has been captured in its entirety, which in turn enables the calculation of average concentrations when considering the volume of water processed by the apparatus. Extracted analytes can be processed by processor 510, where processor 510 may comprise a sensor apparatus (e.g., a gas chromatograph equipped with a suitable detector) and computer processor, such as a personal computer or the equivalent.

Referring now to FIG. 9, an example of a method for enabling the determination of kinetic rates within a fluid of interest without requiring storage and analysis of said liquid is shown. The invention enables the miniaturization of diagnostic equipment such as in situ microcosm arrays (ISMAs) and in vivo microcosm arrays (IVMAs). In one embodiment, a method for enabling the determination of kinetic rates within a fluid of interest includes directing fluid flow 601 exiting a test bed 650 to a multi-port switching valve 600. The multi-port switching valve 600 is controlled to switch the fluid to a plurality of channels A, B, C etc., wherein the plurality of channels includes at least two channels. Each of the plurality of channels is connected to at least one in-flow extraction cartridge 602. Analytes of interest from the fluid flow are concentrated in the at least one in-flow extraction cartridge 602. The at least one in-flow extraction cartridge 602 may advantageously contain at least one extraction medium 604 for capturing the analytes of interest. As described below, rates are determined by (i) sequentially channeling the fluid through the extraction flow paths where each flow path receives fluid for a pre-selected time duration, (ii) retrieving the charged extraction cartridges, (iii) analyzing the extraction cartridges, and computing the kinetic rate of interest.

In one example embodiment analytes are trapped on the extraction media and the fluid, depleted of the analytes of interest, is emptied into the environment, a temporary holding bladder, or individual effluent bags. In another example embodiment, as best shown in FIG. 11, the kinetic rate of interest comprises the slope of a straight line derived from data analysis of the captured analytes from the extraction cartridges. In another example, the at least one extraction cartridge includes a plurality of extraction media that can be arranged in parallel or in sequence. In another example, labile analytes of interest may advantageously be preserved on the extraction media for stabilization, determination of kinetic rates of interest, without requiring retrieval and analysis of the fluid flow subsamples.

Referring now to FIG. 10, there shown is a system for enabling the determination of kinetic rates within a fluid of interest. Fluid flow 601 exiting a test bed 650 (as shown in FIG. 9) is coupled to a multi-port switching valve 600 controlled by a control unit 630. The switching valve has at least 2 channels A, B, C, etc. Each channel is connected to an in-flow extraction cartridge 602 filled with at least one extraction medium 604, as also shown in FIG. 9, that scavenges (concentrates) analytes of interest from the fluid flow passing through it. Specific analytes of interest can be captured on different in-flow extraction cartridge(s) 602 and extraction media 604 that can be arranged in parallel or in sequence C. Analytes are trapped on the extraction media and the fluid, depleted of the analytes of interest, is emptied into the environment, a temporary holding bladder, or individual effluent bags.

Extracted analytes are processed by processor 510, where processor 510 may comprise a sensor apparatus (e.g., a gas chromatograph equipped with a suitable detector) and computer processor, such as a personal computer or the equivalent. Rates are determined by the method of (i) sequentially channeling the fluid through extraction flow paths A, B, C, etc., (ii) retrieving the charged in-flow extraction cartridge(s) 602 and extraction media 604, (iii) analysis of the in-flow extraction cartridge(s) 602 and extraction media 604, followed by analysis of the data and computation of the kinetic rate of interest, as described in more detail below in FIG. 11. This method enables (i) the preservation of labile analytes of interest on extraction media for stabilization, determination of kinetic rates of interest (ii), and does so (iii) without requiring retrieval and analysis of the fluid flow subsamples.

This method is suitable for significantly reducing the dimensions of existing in situ microcosm array (ISMA) and in vivo microcosm array (IVMA) instrumentation as described in, for example, U.S. Pat. No. 7,662,618, U.S. patent application having publication number 2007/0161076, and US patent application having publication number 2010/0159502, all of which are incorporated herein by reference in their entirety. For example, current embodiments of the ISMA have a length of over 20 feet; much of this length is necessitated as room for storage of liquids. Using the here disclosed method, the length of the ISMA device can be cut into less than a half. Similar benefits are expected for IVMA devices. To prevent short circuiting of liquids, processed fluids can be stored in a bladder in the groundwater monitoring well (ISMA), above ground (ISMA) or in bags within or outside of the body of the carrier of IVMA devices.

Referring now to FIG. 11, a hypothetical example of data analysis for the determination of kinetic rates within a fluid of interest is schematically shown. Table 1 below presents hypothetical analysis data from labile analytes of interest extracted from a fluid sample as may be preserved of on extraction media. Curve 505 is a plot of measurements of the values of Table 1 along a time line of arbitrary units. In the example, the kinetic rate is proportional to the slope of curve 505, which follows zero-order kinetics. If the data presented in the middle column of Table 1 would represent logarithmically transformed values (right column), then a plot of the values vs. time would represent a semi-log plot. The resultant slope of the straight line obtained then would represent the rate coefficient of a first-order reaction. Other kinetic reaction orders including second-order and mixed order could result from different data, as is evident for those skilled in the art. FIG. 12 illustrates a hypothetical logarithmic data plot 605.

It may be advantageous to measure the values shown in Table 1 in real-time using a real-time sensor. The information obtained would be immediately available but would be of no or little regulatory value because the data were not obtained by a certified laboratory. To increase the value of the measurements obtained, the present invention allows for the collection of samples that can be submitted to a certified laboratory. Thus, the invention has value whether it is used by itself or in combination with a real-time sensor.

TABLE 1

| Time | Value | Log Value |
|------|-------|-----------|
| 0    | 10    | 10        |
| 1    | 9     | 9         |
| 2    | 8     | 8         |
| 3    | 7     | 7         |
| 4    | 6     | 6         |
| 5    | 5     | 5         |
| 6    | 4     | 4         |
| 7    | 3     | 3         |
| 8    | 2     | 2         |
| 9    | 1     | 1         |
| 10   | 0     |           |
| 11   | 0     |           |

Nammo Talley Laboratory Experiment
Site Description

In one experiment, a field demonstration was conducted at an industrial site located east of Phoenix, Ariz. in the arid southwest of the United States. The site has been the location of small explosives manufacturing since the 1960s. Disposal practices at the time have lead to the release of ammonium perchlorate into the soil matrix and groundwater resulting in contamination of both matrices above regulatory limits. The source area for the perchlorate contamination has been identified as a sludge bed and several monitoring wells have been installed.

The soil in the area is characterized by low organic carbon content and is mostly made up of silty sands and gravels, poorly and well graded sands, clayey sands and clayey gravels. The groundwater level is around 175 ft below ground surface and groundwater flow is generally to the southeast.

Experimental Setup—Laboratory Experiment

All laboratory experiments were conducted using the same equipment as used for the field experiments (glass columns, peristaltic pumps, Teflon storage bags, Viton tubing). Microcosms were packed with well graded sediment (0.5-1 mm grain size) obtained during the installation of well HPA-1 in 2009. The sediment had been stored at ambient temperature and was dried prior to processing. Since the sediment contained much higher concentrations of perchlorate contamination than the currently saturated zone in the source area, sediment was washed with site groundwater to remove excess perchlorate. Site groundwater containing about 604 µg/L perchlorate was used as the microcosm influent for laboratory experiments.

Since perchlorate is largely resistant to chemical treatment in situ and previous tests had shown a very low population of anaerobic microbes in native sediment at the site, experiments focused on bioaugmentation tests. The following experiments were conducted in the laboratory: 1) site sediment without amendment simulating monitored natural attenuation (MNA); 2) bioaugmentation with sewage sludge and biostimulation with ethyl lactate (carbon source and electron donor); 3) bioaugmentation with sewage sludge and biostimulation with sodium acetate (carbon source and electron donor). All experiments were conducted in triplicate. As a control influent groundwater was collected in the same fashion as microcosm effluent over the duration of the experiment without passing through sediment columns. All experiments were conducted simultaneously using the same source of site groundwater.

For bioaugmentation sewage sludge, obtained from 5 different US wastewater treatment plants, was mixed and amended with perchlorate to stimulate growth of microbes capable of perchlorate reduction. For the purpose of bioaugmentation, 1 mL of sewage sludge was added to each bioaugmentation microcosm at the beginning of the experiment. Ethyl lactate was added at 2.9 mM influent concentration in experiment 2; sodium acetate was added at 8.1 mM in experiment 3. To compare bioaugmentation to the effects of natural attenuation, three columns were operated without addition of carbon source or biomass (experiment 1). All microcosms were operated in up-flow mode at 15 µL/min flow.

The effluent of all microcosms was collected at room temperature in individual storage bags containing a microbial preservative (Kathon®, 0.5 mL/L effluent). In addition, time discrete samples of the effluent were collected periodically, sterile filtered, and analyzed for pH as well as concentration of perchlorate, nitrate, nitrite and sulfate.

After termination of the experiment, composite effluent samples were analyzed for the same parameters, and DNA was extracted from microcosm effluent as well as the column sediment.

Table 2 below lists the experimental data for the various effluents.

TABLE 2

| Perchlorate   | bypass [ug/L] | Conc. (final) [ug/L] | Time lapsed [days] | Rate k [ug/L-day] |
|---------------|---------------|----------------------|--------------------|-------------------|
| Na acetate    | 492           | 0.01                 | 2                  | 246               |
|               | 492           | 0.01                 | 2                  | 246               |
|               | 492           | 0.01                 | 2                  | 246               |
|               | 615           | 0.2                  | 21                 | 29.3              |
|               | 548           | 10.3                 | 21                 | 25.6              |
|               | 682           | 6.5                  | 21                 | 32.2              |
| Ethyl lactate | 492           | 0.01                 | 4                  | 122.9             |
|               | 492           | 0.01                 | 4                  | 122.9             |
|               | 492           | 0.01                 | 4                  | 122.9             |
|               | 615           | 13.3                 | 21                 | 28.7              |
|               | 548           | 12.9                 | 21                 | 25.5              |
|               | 682           | 40.5                 | 21                 | 30.5              |
| MNA           | 615           | 568                  | 21                 | 2.3               |
|               | 548           | 420.5                | 21                 | 6.1               |

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A method for contaminant mass collection in saturated sedimentary environments for bioavailability determination, the method comprising:
   securing a screen casing around a shell to form an in situ device, where the screen casing provides a permeable interface between a sampled environment and the shell;
   installing a first water intake within the screen casing, where the screen casing is in fluid communication with the first water intake;
   installing a second water intake within the casing, where the second water intake is vertically spaced apart from the first water intake;
   coupling at least one multi-channel pump to pump water flowing through the first water intake and the second water intake through separate pump channels;
   coupling sorptive media to receive water from the at least one multichannel pump;
   where the water includes a sample environment having bulk water at a first layer and sediment pore water at a second layer, deploying the first water intake in the first layer and the second water intake in the second layer; and
   operating the pump to draw bulk water from the first water intake and to draw pore water from the second water intake, simultaneously or sequentially, for a series of specified time increments to arrive at a time-averaged concentration of analytes from the first layer and the second layer of the sampled environment in the sorptive media, where the concentrated analytes include the analyte mass of time-weighted fluid samples.

2. The method of claim 1 wherein the sorptive media are contained in at least two extraction cartridges which are connected in series or parallel to one or more outputs of the pump.

3. The method of claim 1 wherein deploying the in situ device comprises vertically deploying the in situ device.

4. The method of claim 3 wherein vertically deploying the in situ device comprises using direct-push deployment or augering.

5. The method of claim 1 further comprising first filtering the water entering the device.

6. The method of claim 1 wherein the sorptive media is selected to simulate uptake of pollutants into biological organisms.

7. The method of claim 1 wherein operating the pump to concentrate analytes includes collecting depth-discrete samples from pore water corresponding to saturated sediments in the sampled environment.

8. The method of claim 7 including time-averaged collection of said samples over arbitrary periods of time, and analysis of transport phenomena.

9. The method of claim 2 wherein deploying the in situ device comprises placing the in situ device in a saturated sediment within the sampled environment until interstitial water between the screen and the casing of the in situ device is in equilibrium with the pore water of the saturated sediment, and activating the pump to pass the water through the sorptive media.

10. The method of claim 9 including operating the pump continuously at flow rate so that withdrawn water is replaced in the interstitial volume by pore water.

11. The method of claim 9 including operating the pump intermittently so as to pass the entire volume of the interstitial water through the extraction cartridges.

12. The method of claim 1 wherein the concentrated analytes includes a concentration of pollutants affecting sediment-dwelling biota.

13. The method of claim 1 further comprising measuring a contaminant ratio of bulk water to pore water.

14. The method of claim 13 further comprising determining of pollutant concentrations in pore water and pollutant concentrations in bulk water combined with analyzing of resident, sediment dwelling biota and resident bulk-water dwelling biota; and calculating approximate pollutant concentrations in biota living in sediment and bulk water, respectively.

15. The method of claim 13 further comprising predicting a level of exposure for organisms in contact with both bulk water and sediment pore water by computing an additional bioaccumulation factor to predict their level of exposure and body burden.

16. The method of claim 1 wherein pore water taken into the in situ device is fractionated into (i) unfiltered pore water, (ii) filtered pore water, and (iii) ultra-filtered, colloid-depleted pore water.

17. The method of claim 1 further comprising using selected extraction resins in parallel to extract contaminant groups from the water including ionic and non-ionic analytes.

18. The method of claim 17 further comprising elution of the extracted contaminant groups followed by toxicity assays.

19. The method of claim 1 wherein the screen casing is a mesh sleeve.

* * * * *